United States Patent [19]

Harrison

[11] Patent Number: 4,823,811

[45] Date of Patent: Apr. 25, 1989

[54] ELECTROSTATIC DEEP HEATING APPLICATOR

[75] Inventor: William H. Harrison, Malibu, Calif.

[73] Assignee: Donald L. Morton & Associates, Los Angeles, Calif.

[21] Appl. No.: 6,219

[22] Filed: Jan. 23, 1987

[51] Int. Cl.⁴ .............................................. A61N 1/40
[52] U.S. Cl. ................................. 128/804; 219/10.81
[58] Field of Search ................................ 128/804, 1.5; 219/10.81, 10.79, 10.55 R; 600/10

[56] References Cited

U.S. PATENT DOCUMENTS

| 2,044,257 | 6/1936 | Patzhold et al. | 128/804 |
| 4,672,980 | 6/1987 | Turner | 128/804 |
| 4,702,262 | 10/1987 | Anderson et al. | 128/804 |

FOREIGN PATENT DOCUMENTS

| 1177895 | 11/1984 | Canada | 128/804 |
| 807349 | 1/1937 | France | 128/804 |

OTHER PUBLICATIONS

Raskmark et al, "Focused Electromagnetic . . . Tissue", IEEE Trans. MIT-32, No. 8, Aug. 1984, pp. 887–888.
Rutten et al, "A Three Dimensional Model . . .", Int. J. Hyperthermio, 1986, vol. 2, No. 3, pp. 243–252.
Lagendyk, "A New Coaxial TEM . . . ", J. Microwave Power, 1983, (8), pp. 367–375.

Primary Examiner—Lee S. Cohen
Attorney, Agent, or Firm—Poms, Smith, Lande & Rose

[57] ABSTRACT

An electrostatic deep heating applicator deposits RF energy in a relatively uniform manor throughout a given cross-section of the human torso, thus resulting in a similar uniform heating of the region. The applicator uses a pair of identical, rectangular or cylindrical applicators which generate a heat-producing electric field predominantly parallel to the major axis of the body so as to minimize excessive surface heating. The applicator finds particular use in the treatment of deep seated cancers in patients. Its dimensions allow a relatively large circumferential air gap when placed around the torso so that it is convenient to use and is non-threatening to the patient.

10 Claims, 5 Drawing Sheets

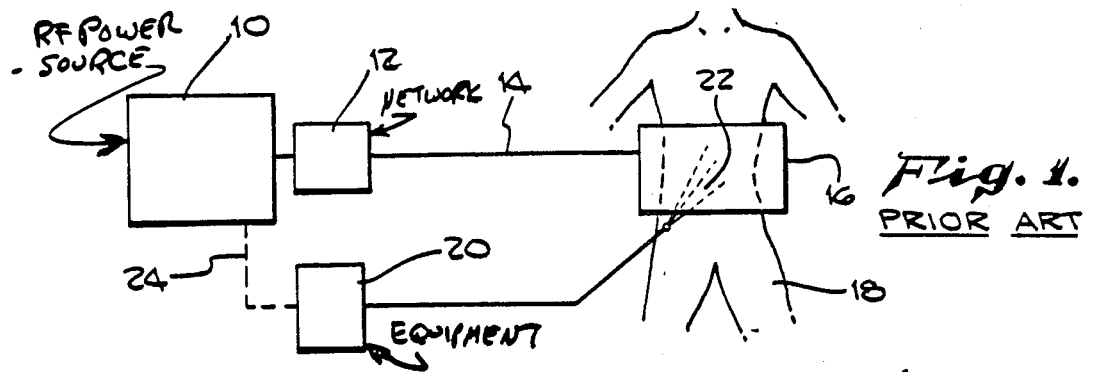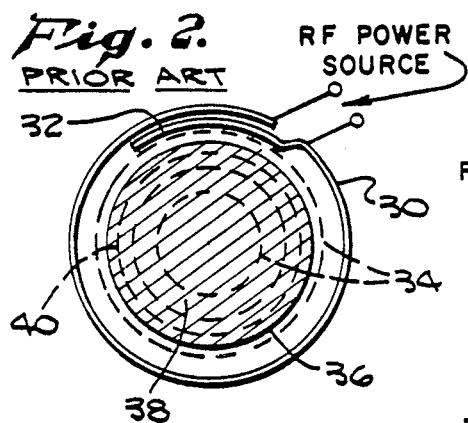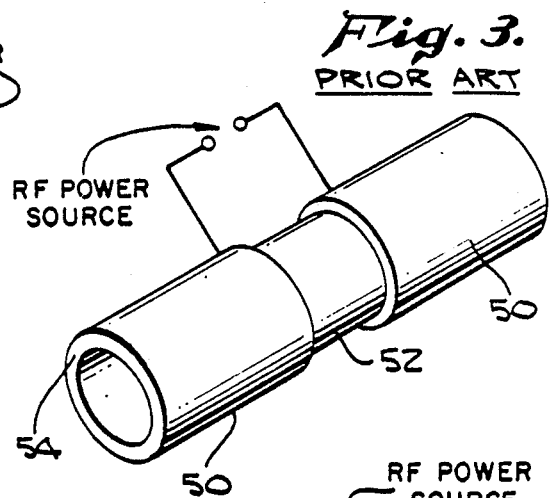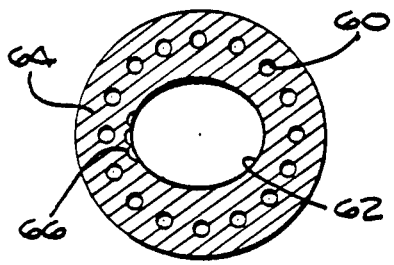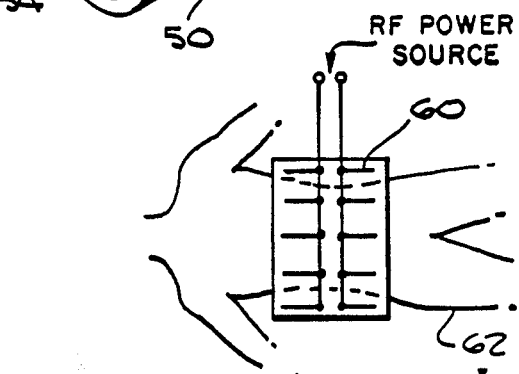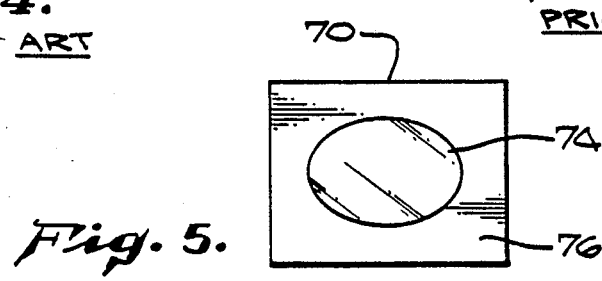

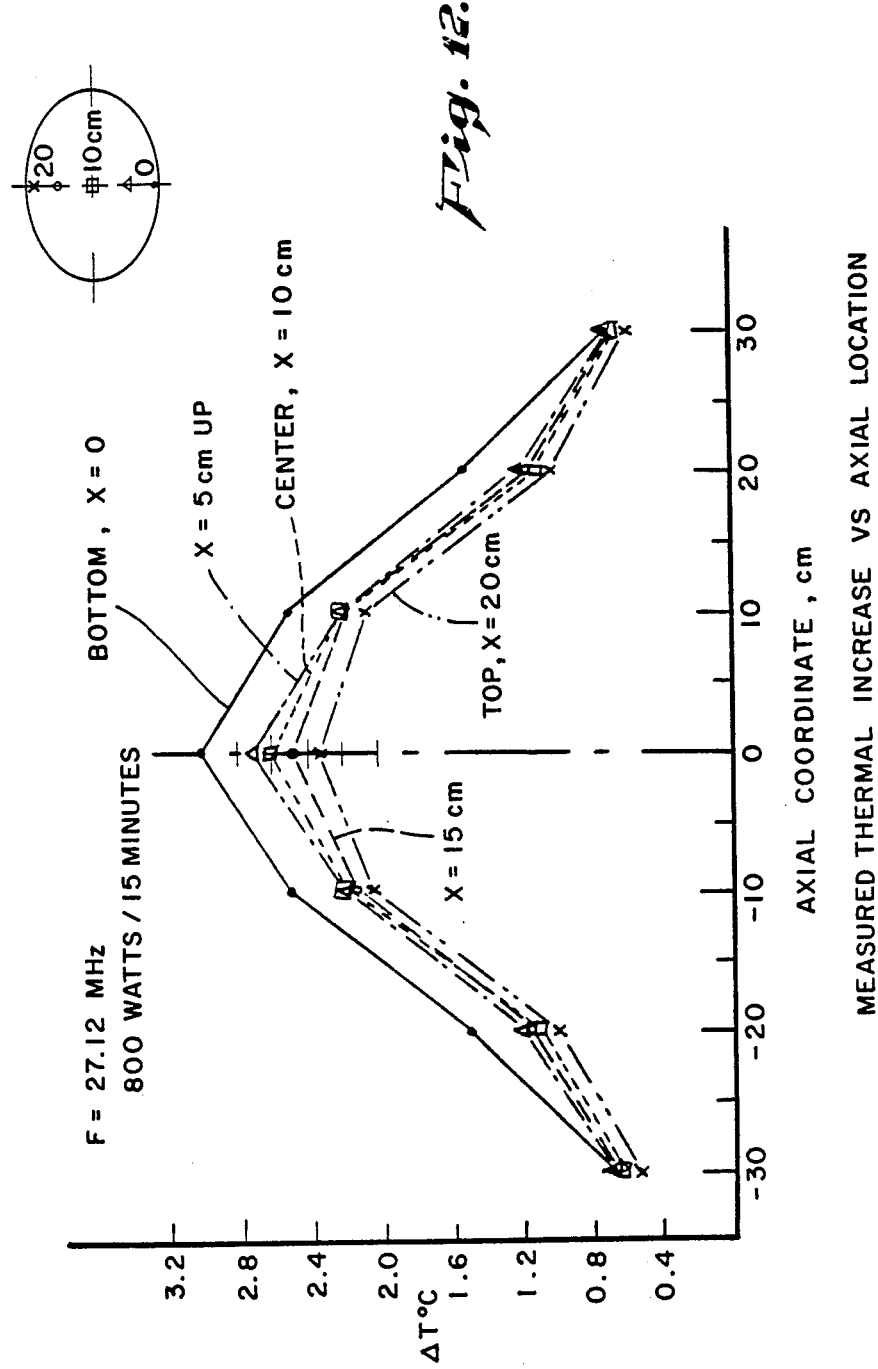

ELECTROSTATIC DEEP HEATING APPLICATOR

FIELD OF THE INVENTION

The present invention relates generally to hyperthermia treatment of tumors and specifically to the selective and uniform depositing of RF energy during such treatment.

BACKGROUND OF THE INVENTION

Heating of cancerous tumors is now recognized as a valuable adjunct to the long established treatment with chemotherapy or radiotherapy because the treatment effectivity is often enhanced when hyperthermia is included as part of the protocol. It is thus desirable to elevate the tumor temperature as much as possible without causing injury to healthy tissue during the hyperthermia treatment.

Effective heating of a tumor deep within the body, say at 8 to 10 cm depth, has been a goal of many applicator designers. This is very difficult to achieve, however, and is always limited by the allowable temperature elevation of healthy tissue at lessor depths as well as at the muscle-fat interface or at the surface itself.

An overview of a prior art hyperthermia system used to heat tumors in the torso of the body is illustrated in the block diagram of FIG. 1. An RF power source 10 typically provides 400–1000 watts, which is coupled via a matching network 12 and a transmission line 14 to the applicator 16, thence to the torso of the patent 18. Thermometry equipment 20 is connected to the patient to monitor temperature at various locations via fiber-optic probes 22. This thermal information can also be used to control the amplitude of the RF power source through a feed back loop 24 if desired.

Various applicators have been successfully devised to heat tumors. However, heating has most consistently been achieved in surface or near surface tumor therapy where the overlying tissue is not a basic limitation. The design of applicators for this type of therapy are relatively straightforward and often operate at microwave frequencies where some focussing can be achieved. Other applicators that are more specifically designed for deep heating have also been developed. These devices generally operate in the lower HF or VHF frequencies where greater depth of penetration is possible. Several relevant devices of this type are illustrated in FIGS. 2, 3, and 4, and discussed in the literature.

They are:

1. "Deep Heating Electrode," Harrison, U.S. Pat. No. 4,186,729;
2. "Focused Electromagnetic Heating of Muscle Tissue," IEEE Trans. MIT-32, #8, August, 1984, pages 887–888;
3. "Annular Phased Array," IEEE Trans. BME-31, pages 106–114, January, 1984;
4. "A Three-Dimensional Model For the Coaxial TEM Deep-Body Hyperthermia Applicator," Int.J.Hyperthermia, 1986, Vol. 2, No. 3, pages 243–252; and
5. "A New Coaxial TEM Radiofrequency/Microwave Applicator For Non-Invasive Deep-Body Hyperthermia," Journal of Microwave Power, 1983, 18, pages 367–375.

These devices are capable of penetrating the subcutaneous layers and heating imbedded tumor tissue without serious surface overheating. However, each has its limitations.

1. The patent entitled "Deep Heating Electrode," U.S. Pat. No. 4,186,729, illustrated in FIG. 2 consists of a single turn, resonant, non-contacting cylinder 30 that surrounds the body and does not require bolus (water bags) between the electrode and the patient. The conducting sheet forms the inductor 30 and the overlapping sheets form the capacitor 32 required to resonate the circuit. The device typically operates on the lower ISM frequencies, i.e., 13.56, 27.12 or 40.68 MHz. When fed from an RF power source, the resulting induced concentric electric field lines 34 are parallel to the body surface 36 and energy deposition in the deep muscle tissue 38 is not dependent upon electric field lines that must pass through the fat/skin layer 40. Clinical experience with over 1000 patients shows that excessive surface heating is spared and deep heating is often achieved.

However, the concentric electric field strength is proportional to the radius, thus heating is also dependent upon the relative radial location. Calculations and experience have shown that the halfpower depth of penetration is typically 6 to 7 cm below the surface of the the torso with a patient having a 1 to 2 cm fat layer.

2. The paper "Focused Electromagnetic Heating of Muscle Tissue, MIT-32" describes an applicator, as shown in FIG. 3, that consists of two identical metallic cylinders 50 spaced from one another and placed concentrically over a cylindrical phantom simulating muscle tissue 52 to be heated. A very thin 2 mm insulator 54 is placed between the phantom and the metallic cylinders. The cylinder diameter, phantom dimensions and frequency of operation are chosen to obtain construction interference in the central region of the limb/phantom to be heated. For the case cited in this paper, this approach requires an RF power source operating at a frequency of 150 MHz.

The object of the concept illustrated in FIG. 3 is to select a frequency and radial dimension so as to create a radial standing wave in the tissue where the diameter is an even multiple of one-half wavelength in the muscle equivalent tissue. The dielectric constant of muscle tissue is on the order of 80 to 100, thus the wavelength is reduced by the square-root of this value. The electric field from opposite sides is thus reinforced in the central region where preferential localized central heating can occur. The concept is acceptable when working with an experimental uniform cylindrical phantom 52 as shown in FIG. 3. However, the approach has serious limitations when dealing with the shape irregularities of a human torso where the required minimum spacing to the body cannot be maintained and this compromises the necessary radial phase relationship. As discussed therein, a 10 cm diameter phantom was used, with just 2 mm spacing between the phantom and the cylindrical metallic shells, i.e., a very precise spacing not achievable in a clinical environment.

3. The device in the paper "Annular Phased Array," is illustrated in FIG. 4 and consists of a group of as many as 16 dipole elements 60 that are radially spaced around the patient's torso 62 and fed in phase from a common RF source. To obtain sufficient RF coupling to the body, distilled water bags 64 are placed between the dipoles and the patient. This allows the dipole elements to function in a medium having a dielectric constant similar to muscle tissue (approximately 78), thus enhancing the coupling and minimizing the discontinuity between the dipole elements and the body surface. By carefully filling all the voids 66 between the dipole elements and the patient with water bags, efficient RF energy transfer and heating can be achieved at depth.

From a human usage point of view, this device also has serious limitations. It is very difficult to achieve uniform filling of the voids around the patient with water bags. Variable fat thickness, with its lower dielectric constant, also creates additional discontinuities. When these variations occur, localized hot spots will exist that can cause injury or limit the extent of energy input possible without localized thermal damage. It is also very time consuming to properly position the water bags and check for localized heating before treatment begins, thus contributing to patient fatigue and degraded treatment tolerance.

4. The device disclosed in the paper "A Three-Dimensional Model For The Coaxial TEM Deep-Body Hyperthermia Applictor" develops a very detailed three dimensional mathematical model showing that deep heating is possible using a pair of cylindrical sleeves as described above.

5. The device disclosed in the paper "A New Coaxial TEM Radiofrequency/Microwave Applicator For Non-Invasive Deep-Body Hyperthermia" provides a limited theoretical evaluation of the same model showing that the applicator will work with human body dimensions and verifies these predictions with a small model operating at an appropriately scaled higher frequency.

The various prior art devices described above have the limitation of being close fitting around the object heated or using a water bolus to fill the void between the applicator and object to be heated. The IJH paper concludes, "For an efficient electromagnetic coupling, a sufficiently cooled water bolus between the aperture and the human body is necessary." The JMP paper concludes, "To match the patient to the applicator aperture, a distilled water bolus between the patient and the applicator aperture is necessary."

Prior Art devices 2 through 5 are not resonant devices and a serious impedance mismatch with the 50 ohm line to the RF power source will result unless a water bolus is used as described. Moreover, the lack of a resonant structure limits the frequencies which may be employed in the devices.

Accordingly, it is the principal object of the present invention to deposit RF energy in a uniform manner in tissue.

It is another object of the present invention to treat tumors by hyperthermia treatment without the need for a water bolus or an applicator closely fitting around the patient.

Yet another object of the invention is to allow an applicator to function at various frequencies and to optimally couple the RF energy to the applicator.

SUMMARY OF THE INVENTION

The present invention, in a broad aspect, includes a pair of identical metallic cylindrical or rectangular applicator sleeves spaced along the torso. The applicator sleeves are resonated with an inductor.

The sleeves are well spaced from the body (radial spacing) and do not require the use of a water bolus between the applicator and the patient. This is possible because the sleeves become part of the resonant circuit employed to raise the impedance of the applicator and obtain the necessary coupling to the torso without a water bolus between the patient and applicator. The resonant circuit also becomes a part of the matching circuit that precisely matches the cylinder impedance to the 50 ohm RF power source. To work on different frequencies, it is simply necessary for the present device to be re-resonated at the new desired frequency by changing the L/C values in the circuit.

The measured thermal response of the present invention shows relatively uniform heating at depth in cross-sections equivalent to that of the human torso.

Additional inductive and capacitive loading can be employed to eliminate any E-field asymmetry or resonance sensitivity.

A beneficial method of providing uniform heating is also provided with the invention.

Other objects, features, and advantages of the present invention will become apparent from a consideration of the following detailed description and the accompanying drawings.

BRIEF DESCRIPTION OF THE DRAWINGS

FIG. 1 is a schematic block diagram of a prior art hyperthermia system designed to heat the torso of the body;

FIG. 2 is a cross-sectional view of a prior art applicator employing a single turn resonant cylinder with a magnetic induction technique of heating the torso;

FIG. 3 is a perspective view of a prior art applicator employing two close fitting sleeves where the diameter and frequency of operation are chosen to establish a reinforced radial standing wave in the center of the phantom being treated;

FIGS. 4(a) and (b) illustrate a prior art applicator using a series of radial dipole elements inserted in water bags that are in contact with the patient;

FIG. 5 is an end view of an electrostatic deep heating applicator according to the present invention;

FIG. 11 is a graph showing the measured thermal pattern in an experiment employing the present invention as observed in a muscle equivalent phantom of the torso having the same cross-section as used in E-field measurements of FIG. 10; and FIG. 12 is a similar measurement as that shown in FIG. 11 where the duration of heating has been increased to obtain a more pronounced temperature increase.

DETAILED DESCRIPTION

Referring more particularly to the drawings, a new applicator, as shown in FIGS. 5-9, has been developed that deposits RF energy in a nearly uniform manor throughout a cross-section of the human torso without the undesired characteristics of the previous devices described.

Figure 7:
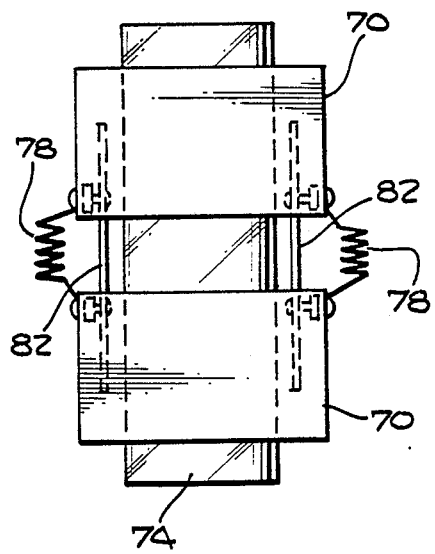
FIG. 7 is a top view showing an alternative embodiment of the present invention.
Figure 6:
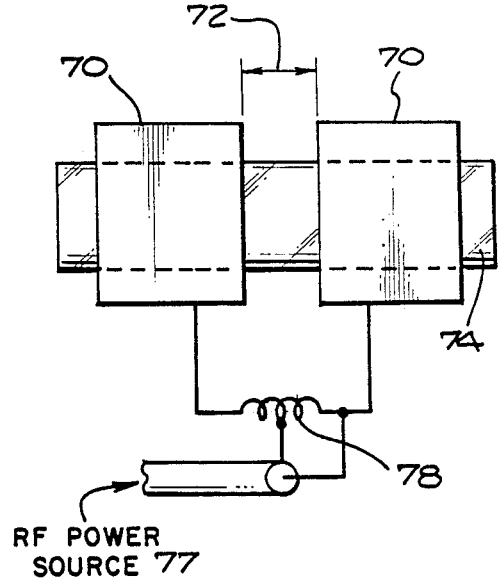
FIG. 6 is a top view of an electrostatic deep heating applicator system according to the present invention.

The basic applicator system and the method relating thereto, as shown in FIGS. 5 and 6, consists of two identical metallic rectangular sleeves 70, spaced from one another by a gap 72. Other shapes, such as cylindrical, elliptical, or square could be used. They are placed concentrically around the torso-simulating phantom 74. As will be shown, heating occurs principally in the gap region between the two sleeves. The sleeves dimensions (width and height) are typically 30% to 50% greater than the torso so that the applicator sleeves allow a relatively large air gap 76 to exist between the patient and the metallic sleeves.

The two sleeves 70 surrounding the torso 74 are electrically connected to each other, in the example, by a coil 78. The inductance of the coil and the capacity developed between the sleeves and the torso form a resonant circuit through which RF power 77 can be applied as shown. The RF energy can be coupled directly to the sleeves by an impedance matching circuit and a balun, by tap coupling of the RF energy through one of the inductors, (as shown in FIG. 6) or by tap coupling of the RF energy employing the shield plates discussed below as a ground return.

Even though the sleeves surrounding the torso are small in terms of wavelength, a non-uniform E-field distribution occurs in the phantom cross-section if the two sleeves are simply resonated with an inductor attached at a single point to each sleeve as shown in FIG. 6. The resonant condition produced by the sleeve/torso capacity and inductor is also sensitive to movement and torso size.

Figure 8:
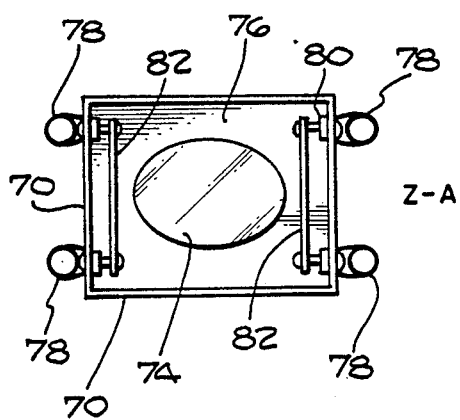
FIG. 8 is an end view of the embodiment shown in FIG. 7.
Figure 9:
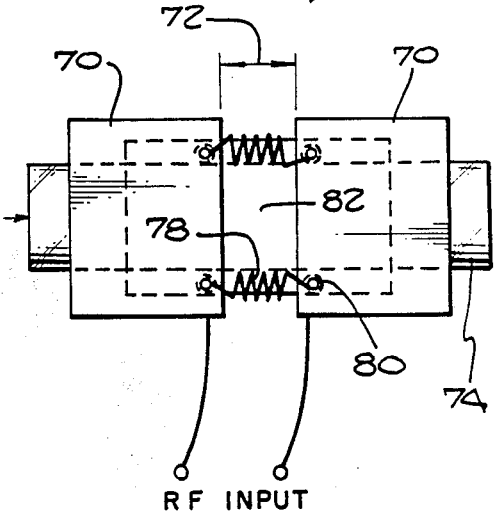
FIG. 9 is a side view of the embodiment shown in FIG. 7.

Any E-field asymmetry and resonance sensitivity can be corrected by the proper placement of additional inductive and capacitive loading as shown in the alternative embodiment of the invention depicted in FIGS. 8 and 9. The two sleeves 70 surrounding the torso 74 are electrically connected, in the figures, by four coils 78 in conjunction with eight identical capacitors 80 and two shield plates 82. The shield plates 82 are placed along both sides of the applicator between the phantom and the applicator sleeves. Electrically, the shield plate surfaces form equal capacitance to both sleeves so that a neutral RF potential exists on the shield plates, i.e., they are at ground potential. By positioning the plates as shown in the figures, the E-field level around the minor axis of the elliptical phantom was reduced to a level equal to that established elsewhere.

The addition of the coils and fixed capacitors are arranged so that the field distribution around the sleeves is very uniform. Likewise, the added capacitive loading stabilizes the resonant circuit so that it is not significantly affected by patient to patient variation.

In a prototype of the present invention, the circuit was resonated at 27.12 MHz. This frequency resulted in convenient inductor and capacitor values and good coupling to the torso was possible. Since 27.12 MHz is also an ISM frequency, its used does not require a screen room to further minimize RF radiation. The same applicator principles however can be used at other frequencies by proper choice of the circuit element values.

Figure 10:
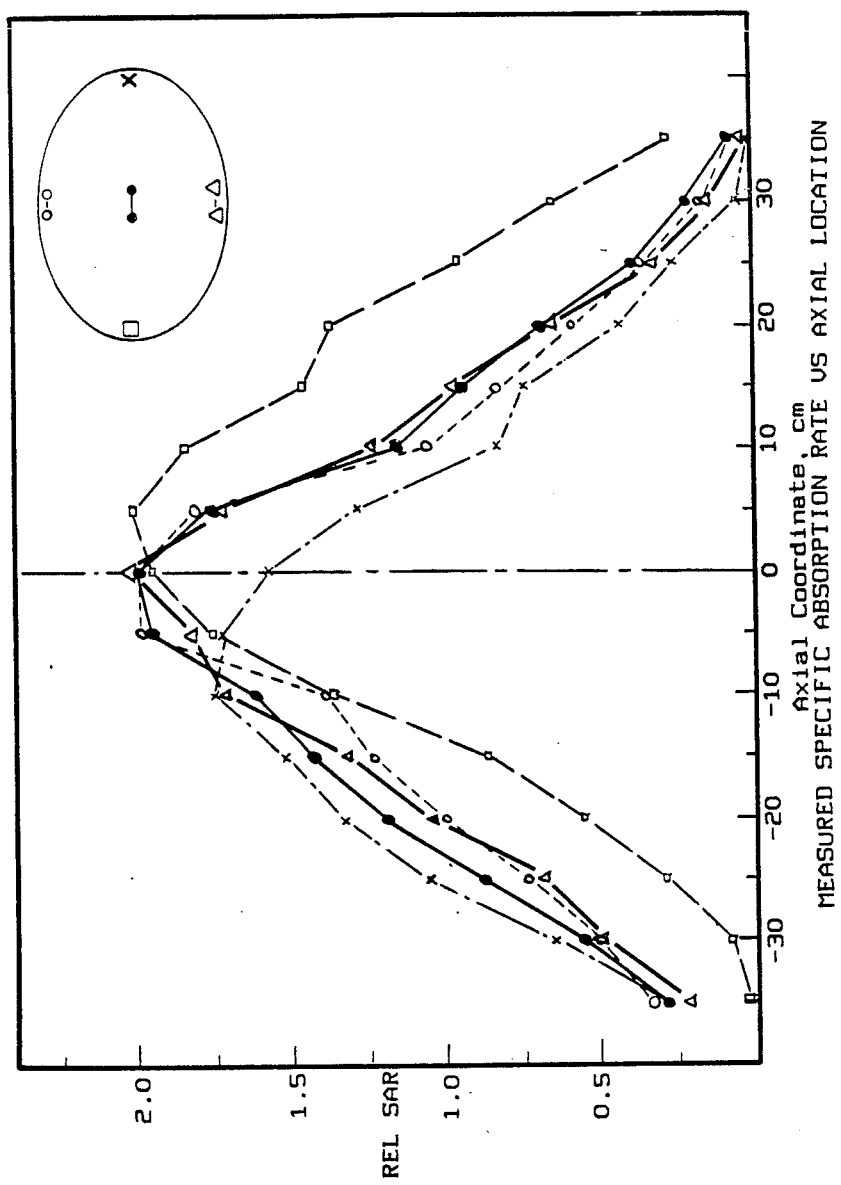
FIG. 10 is a graph showing the measured relative electric field strength in an experiment employing the present invention as observed in a saline water tank designed to simulate the cross-section and conductivity of the human torso.
Figure 14:
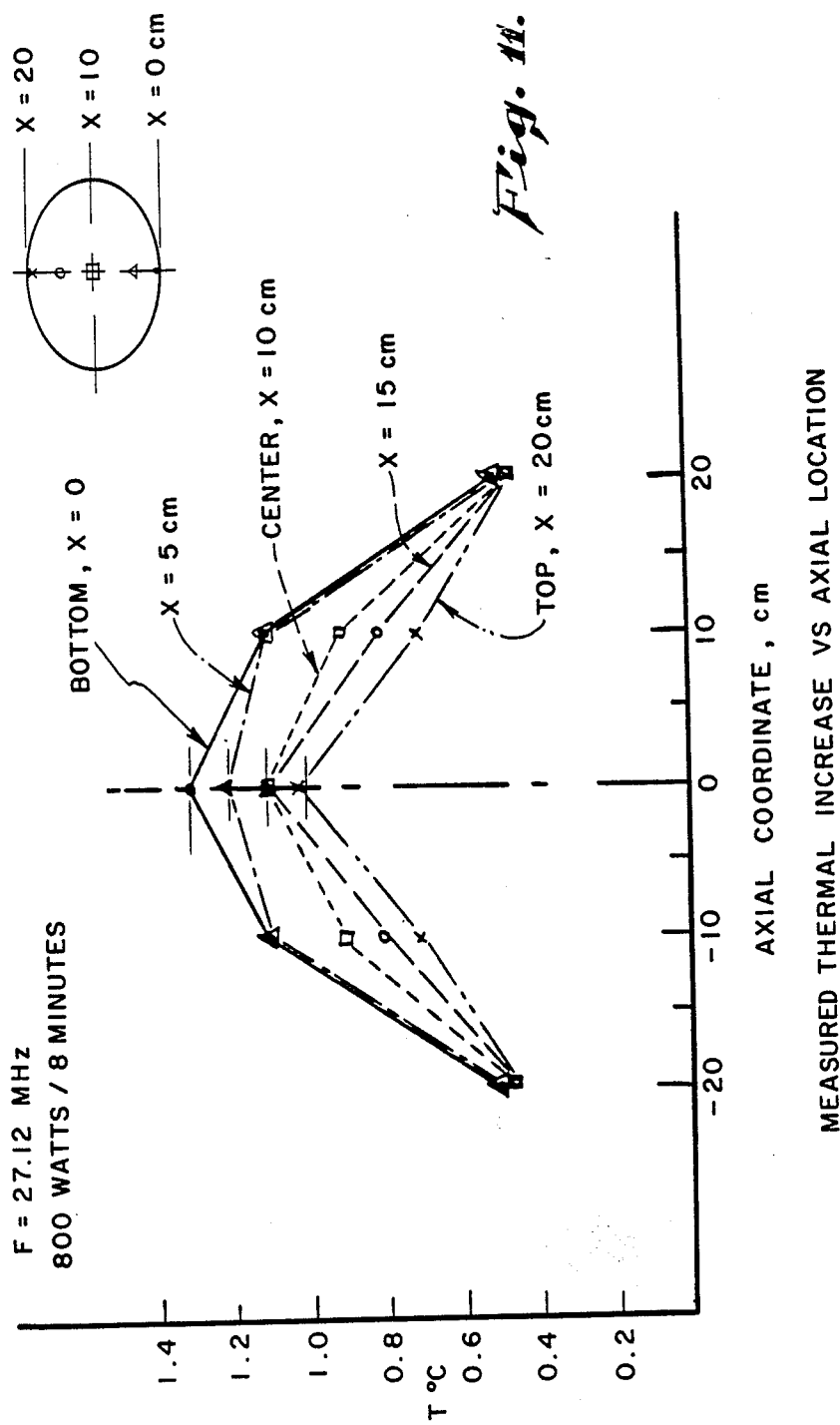

The elongated elliptical cross-section phantom 74 was used to make RF E-field and thermal measurements in a saline tank with the new applicator because it more nearly duplicated the human torso. The resulting electric field pattern was measured as shown in FIG. 10. Differences in the right and left side field-strength response shape may be seen. However, since the levels did not exceed that produced in the center, it is not considered a problem.

FIG. 10 was plotted in terms of the relative Specific Absorption Rate, SAR. The tank was filled with a saline solution where the salt content was adjusted to provide the approximate conductivity of human muscle tissue at 27 MHz, i.e., 0.62 mhos per meter.

The corresponding heating patterns for two different heating times are shown in FIGS. 11 and 12 and the plots represent the measured thermal increase. The thermal patterns were measured in the same tank as used for the E-field measurements but with the tank filled with finely powdered silicon saturated with a saline solution. Again, the required salinity was experimentally determined, by measurement, to produce a phantom conductivity equivalent to muscle tissue.

FIG. 11 shows the thermal response after applying 800 watts for 8 minutes. FIG. 12 shows that a similar heating pattern was obtained when the duration was increased to 15 minutes. As is shown, relatively uniform heating is obtained at any depth in the desired cross-section. The thermal increase in the center of the phantom was approximately 15% less than that obtained at the bottom surface, but it was also about 10% greater than that at the top surface.

The relative SAR E-field measurements of FIG. 10 shows that a centrally located tumor (at 10 cm depth) would receive essentially the same SAR within measurement accuracy as that observed at the top and bottom surfaces, i.e., a very uniform excitation pattern that should result in a uniform heating pattern; the object of this invention.

The thermal differences noted in FIGS. 11 and 12, while minor when compared to other methods of heating, appear to be due to an inadvertent variation in the conductivity of the phantom material. Following the thermal experiments, sample conductivity measurements were made as follows: top—0.50 mhos/m, center—0.68 mhos/m and bottom surface—0.85 mhos/m.

It is important to note that maximum heating occurred in the material having the higher conductivity of muscle tissue. This characteristic is a very desireable feature since it discriminates against the heating of fat; a lower conductivity tissue that often heats excessively while attempting deep heating.

In the foregoing description of the present invention, a preferred embodiment of the invention has been disclosed. It is to be understood that other mechanical and design variations are within the scope of the present invention. Accordingly, the present invention is not limited to the particular arrangement which has been illustrated and described herein.

What is claimed is:

1. An electrostatic deep heating applicator for tissue in the body, comprising:

a pair of conductive sleeve means for surrounding said tissue, said sleeve means being adapted to be disposed axially along said body to form a gap for depositing RF energy to said tissue, and each of said sleeve means and said body defining an annular air space of distributed capacitive reactance such that said applicator is loosely coupled to said tissue; and inductor means, attached to said sleeve means and adapted to be coupled to a source of RF energy, for resonating the resonant circuit defined by said sleeve means, said capacitive reactance, said body, and said inductor means to establish an electric field across said gap and currents in said tissue, whereby said currents caused preferential and uniform heating in said gap.

2. An applicator as defined in claim 1, wherein said sleeve means comprises a metallic sleeve having a circular cross-section.

3. An applicator as defined in claim 1, wherein said sleeve means comprises a metallic sleeve having a rectangular cross-section.

4. An applicator as defined in claim 1, wherein said sleeve means comprises a metallic sleeve having an elliptical cross-section.

5. An applicator as defined in claim 1, wherein said applicator further comprises control means for controlling the distribution of said field in said tissue and the sensitivity of said resonant circuit.

6. An electrostatic deep heating applicator for tissue in the body, comprising:
   a pair of conductive sleeve means for surrounding said tissue, said sleeve means being adapted to be disposed axially along said body to form a gap for depositing RF energy to said tissue, and each of said sleeve means and said body defining an annular air space of distributed capacitive reactance such that said applicator is loosely coupled to said tissue; and
   inductor means, attached to said sleeve means and adapted to be coupled to a source of RF energy, for resonating the resonant circuit defined by said sleeve means, said capacitive reactance, said body, and said inductor means to establish an electric field across said gap and currents in said tissue, whereby said currents cause preferential and uniform heating in said gap; and
   control means for controlling the distribution of said currents in said tissue, said control means including capacitor means, coupled to said inductor means, for capacitively loading said circuit, and a plurality of shield plate means disposed adjacent said sleeve means, for further stabilizing said circuit.

7. An applicator as defined in claim 6, wherein:
   said sleeve means comprises a rectangular metallic sleeve;
   said inductor means comprises a multiple inductors, connected between corresponding sides of said sleeves;
   said capacitor means comprises multiple capacitors mounted pair-wise on said multiple inductors; and
   said shield plate means comprises a pair of elongated shield plates disposed in facing relation on opposing sides of said sleeves.

8. An applicator as defined in claim 6, wherein said inductor means includes means for coupling said RF energy to said sleeve means.

9. An applicator as defined in claim 8, wherein said means for coupling comprises an impedance matching circuit adapted to be coupled between said inductor means and said RF energy source.

10. A method of uniformly heating tissue in the body comprising the steps of:
   placing said tissue in non-contacting relationship within a pair of conductive sleeve means for forming a gap for depositing RF energy to said tissue, said sleeve means being disposed axially along said body to form said gap, and each of said sleeve means and said body defining an annular air space of distributed capacitive reactance such that said pair of sleeve means is loosely coupled to said tissue;
   exciting said sleeve means with radio frequency energy to establish an electric field across said gap and currents in said tissue, whereby said currents cause preferential and uniform heating in said gap; and
   resonating said sleeve means to couple said energy to said sleeve means at a selected resonant frequency.

* * * * *